US006204434B1

(12) United States Patent
Bloksberg et al.

(10) Patent No.: US 6,204,434 B1
(45) Date of Patent: *Mar. 20, 2001

(54) MATERIALS AND METHODS FOR THE MODIFICATION OF PLANT LIGNIN CONTENT

(75) Inventors: Leonard N. Bloksberg; Ilkka Havukkala, both of Auckland (NZ); Alastair Grierson, Middlewich (GB)

(73) Assignees: Genesis Research & Development Corporation Limited; Fletcher Challenge Forests Limited, both of (NZ)

( * ) Notice: Subject to any disclaimer, the term of this patent is extended or adjusted under 35 U.S.C. 154(b) by 0 days.

This patent is subject to a terminal disclaimer.

(21) Appl. No.: 09/211,710

(22) Filed: Dec. 14, 1998

Related U.S. Application Data

(63) Continuation-in-part of application No. 08/713,000, filed on Sep. 11, 1996, now Pat. No. 5,850,020.

(30) Foreign Application Priority Data

Sep. 10, 1997 (NZ) ..................................... PCT/NZ97/00112

(51) Int. Cl.[7] .......................... C12N 15/00; C12N 15/29; C12N 15/82; A01H 4/00; A01H 5/00
(52) U.S. Cl. ......................... 800/290; 800/298; 800/278; 800/295; 536/23.6; 536/24.1; 435/417; 435/468
(58) Field of Search .................................. 800/295, 298, 800/278, 290; 536/23.6, 24.1; 435/419, 468

(56) References Cited

U.S. PATENT DOCUMENTS

| 5,122,466 | * | 6/1992 | Stomp et al. | ...................... | 435/172.3 |
| 5,451,514 | * | 9/1995 | Boudet et al. | ........................ | 800/205 |
| 5,850,020 | * | 12/1998 | Bloksberg et al. | ................... | 800/205 |

FOREIGN PATENT DOCUMENTS

| 0513884 | 11/1992 | (EP) | ............................. | C12N/15/11 |
| 0516958 | 12/1992 | (EP) | ............................. | C12N/15/54 |
| 0632128 | 1/1995 | (EP) | ............................. | C12N/15/53 |
| 0716147 | 6/1996 | (EP) | ............................. | C12N/15/82 |
| 4330285 | 11/1992 | (JP) | ............................. | C12N/15/60 |
| 9173069 | 7/1997 | (JP) | ............................. | A01H/1/00 |
| 9008828 | 8/1990 | (WO) | ............................. | C12N/15/82 |
| 9305159 | 3/1993 | (WO) | ............................. | C12N/15/53 |
| 9305160 | 3/1993 | (WO) | ............................. | C12N/15/54 |
| 9315599 | 8/1993 | (WO) | ............................. | C12N/15/00 |
| 9324638 | 12/1993 | (WO) | ............................. | C12N/15/82 |
| 9408036 | 4/1994 | (WO) | ............................. | C12N/21/04 |
| 9421794 | 9/1994 | (WO) | ............................. | C12N/15/29 |
| 9423044 | 10/1994 | (WO) | ............................. | C12N/15/82 |
| 9507993 | 3/1995 | (WO) | ............................. | C12N/15/82 |
| 9527790 | 10/1995 | (WO) | ............................. | C12N/15/53 |
| 9620595 | 7/1996 | (WO) | ............................. | A01N/35/02 |
| 9723599 | 7/1997 | (WO) . | | |
| 9745549 | 12/1997 | (WO) | ............................. | C12N/15/82 |
| 9839454 | 9/1998 | (WO) | ............................. | C12N/15/53 |

OTHER PUBLICATIONS

Mackay et al. Mol. Gen. Genet. 247:537–545, 1995.*
Voo et al. Plant Physiol. 108: 85–97, May 1995.*
Hotze et al. FEBS Letters. 374:345–350, Nov. 1995.*
Wagner, A. et al., "Direct Submission", *Genbank Sequence Database*, (Sep. 29, 1996).
Wagner, A. et al., "Isolation and Characterisation of a Cinnamyl–Alcohol Dehydrogenase Gene from *Pinus Radiata*", *Queenstown Molecular Biology Meeting*, New Zealand Forest Research Institute (Aug. 1996).
Atanassova, R. et al. Altered lignin composition in transgenic tobacco expressing O–methyltransferase sequence in sense and antisense orientation, *Plant Jnl.* 8:465–477, 1995.
Chabbert et al., Manipulation of lignin quality in transgenic poplar, *Biotechnol. Pulp. Pap. Ind. Proc. Int. Conf.* 6[th,] pp. 319–322, 1995.
Baucher, M. et al., Higher extractability of lignin in poplar by reducing cinnamyl alcohol dehydrogenase activity, *Somatic Cell Genetics and Molecular Genetics of Trees*, ISBN 0–7923–4179–1, pp. 153–158, 1996.
Boudet A. M. et al., La lignification domestiquee *BioFutur* 158:27–31, 1996.
Boudet A. M. Genes involved in monolignol biosynthesis and their manipulation for tailoring new lignins *Am. Chem Soc. Abstracts of Paper at National Meeting*, No. 1, 1996.
Elkind Y. et al., Abnormal plant development and down–regulation of phenylpropanoid biosynthesis in transgenic tobacco containing a heterologous phenylalanine ammonia–lyase gene *Proc. Natl Acad. Sci. USA* 87:9057–9061, 1990.
Bate, N.J. et al., Quantitative relationship between phenylalanine ammonia–lyase levels and phenylpropanoid accumulation in transgenic tobacco identifies a rate–determining step in natural product biosynthesis, *Proc. Natl. Acad. Sci. USA* 91:7608–7612, 1994.
Kajita S. et al., Alterations in the biosynthesis of lignin in transgenic plants with chimeric genes for 4–coumarate:Coenzyme A ligase *Plant Cell. Physiol.* 37:957–965, 1996.

(List continued on next page.)

*Primary Examiner*—Lynette R. F. Smith
*Assistant Examiner*—Thomas Haas
(74) *Attorney, Agent, or Firm*—Ann W Speckman; Janet Sleath

(57) ABSTRACT

Novel isolated DNA sequences associated with the lignin biosynthetic pathway are provided, together with DNA constructs including such sequences. Methods for the modulation of lignin content and structure in plants and methods for producing plants having altered lignin content and structure, are also disclosed, the methods comprising and incorporating one or more of the polynucleotides disclosed herein into the genome of a plant.

33 Claims, 1 Drawing Sheet

OTHER PUBLICATIONS

Erickson et al., Laccase as a target for decreasing the lignin content in transgenic trees through antisense genetic engineering, *Biotechnol. Pulp Pap. Ind. Proc. 6th Intl. Conf.* pp. 310–314, 1996.

Lagrimini, L M., Wound–induced deposition of polyphenols in transgenic plants overexpressing peroxidase *Plant Physiol.* 96:577–583, 1991.

Liu, T.Y. et al. Lignin contect and composition in tobacco plants with over and under expressed peroxidase, *Supplement to Plant Physiol.* 102:103, 1993.

McIntyre, C.L. et al. Strategies for the suppression of peroxidase gene expression in tobacco. II. In vivo suppression of peroxidase activity in transgenic tobacco using ribozyme and antisense constructs *Transgenic Research* 5:263–270, 1996.

Sikorski, R.S. et al., Yeast centromere vector pRS415 with LEU2 marker, complete sequence, EMBL Accession No. U03449, Jan. 8, 1984.

Yu, L.X. et al. Lycopersicon chilense unknown protein (LC15) mRNA, complete cds, EMBL Accession No. U19099, Oct. 3, 1995.

Grima–Pettenati, J. et al., E. gunnii OMT mRNA for O–methyltransferase, EMBL Accession No. X74814, Dec. 31, 1993.

Poeydomenge O. et al. A cDNA encoding S–adenosyl–L–methionine:caffeic acid 3–O–methyltransferase from eucalyptus, *Plant Physiol.* 105:749–750, 1994.

Raynal et al. *A. thaliana* transcribed sequence; clone PAP790; 5'end similar to cinnamyl alcohol dehydrogenase; *Stylosanthes hmilis,* EMBL Accession No. Z46703, Nov. 18, 1994.

Goffner D. et al., E. gunnii mRNA for cinnamyl alcohol dehydrogenase, EMBL Accession No. X88797, Dec. 31, 1995.

Newman T., et al., 10030 *Arabidopsis thaliana* cDNA clone 143C13T7, EMBL Accession No. T46767, Feb. 11, 1995.

Zhang, X.H. et al., *Pinus taedae* phenylalanine ammonia–lyase (lpPAL) gene complete cds, EMBL Accession No. U39792, Jan. 1, 1996.

Voo, K.S. et al. *Pinus taeda* PT4CL2 4–coumarate–CoA ligase enzyme, mRNA complete cds, EMBL Accession No. U12013, Jul. 27, 1994.

Zhang X.H. et al., *Pinus taeda* xylem 4–coumarate:CoA ligase (lp4CL–1) gene, complete cds, EMBL Accession No. U39405, Jan. 1, 1996.

Davies, K.M. et al. *Malus sp.* mRNA for anthocyanin hydroxylase, EMBL Accession No. X71360, Apr. 27, 1993.

Hrmova M. et al., *Hordeum vulgare* beta–d–glucan exohydrolase, isoenzyme exoII, mRNA, complete cds, EMBL Accession No. U46003, Feb. 29, 1996.

Willekens, H.D. *N. plumbaginifolia* mRNA for catalase (cat3 gene), EMBL Accession No. Z36977, Sep. 7, 1994.

Ritter D. et al., *Gossypium hirsutum* peroxidase mRNA, complete cds, EMBL Accession No. L08199, Dec. 24, 1992.

Meyer K. et al., *Arabidopsis thaliana* ferulate–5–hydroxylase (FAH1) mRNA, completed cds, EMBL Accession No. U38416, Aug. 13, 1996.

Meyer K. et al., Ferulate–5–hydroxylase from *Arabidopsis thaliana* defines a new family of cytochrome P450–dependent monooxygenases *Proc. Natl. Acad. Sci. USA* 93:6869–6874, 1996.

Sewalt, V.J.H., et al. Reduced lignin content and altered lignin composition in transgenic tobacco down–regulated in expression of L–phenylalanine ammonia–lyase or cinnamate 4–hydroxylase *Plant Physiol.* 115:41–50, 1997.

Rech. P. et al., *E. gunii* mRNA for caffeoyl–CoA O–methyltransferase, EMBL Accession No. Y12228, Apr. 8, 1997.

Bachem, C.W.B., et al. Antisense expression of polyphenol oxidase genes inhibits enzymatic browning in potato tubers, *Biotechnology* 12:1101–1105, 1994.

Udagama–Randeniya, P.V. et al., Coniferyl alcohol oxidase: A catechol oxidase? *Trees* 10:102–108, 1995.

Dharmawardhana, D.P. et al., A beta–glycosidase from lodgepole pine xylem specific for the lignin precursor coniferin *Plant Physiol* 107:331–339, 1995.

Database Dissabs, AN97:45741 Dissabs Order No. AARNN14739, Dharmawardhana, D.P. et al. A biochemical and molecular study of lignin biosynthesis (*Pinus contorta, glucosidase, conferin, xylem*).

Bao W. et al. A laccase associated with lignification in loblolly pine xylem *Science* 260:672–674, 1993.

Shiokawa, T. et al., Expression analysis of a cinnamic acid 4–hydroxylase gene from a hybrid aspen, *Populus kitakamiensis, Chem. Abstracts,* vol. 125, No. 13, abstract No. 163462, Sep. 23, 1996.

Dixon, R. A. et al., Metabolic engineering: prospects for crop improvement through genetic manipulation of phenylpropanoid biosynthesis and defense responses—a review, *Gene Papers* 179:61–71, 1996.

Hotze, M. et al., Cinnamate 4–hydroxylase from *Catharanthus roseus,* and a strategy for the functional expression of plant cytochrome $P_{450}$ proteins as translational fusions with $P_{450}$ reductase in *Escherichia coli, FEBS letters* 374:345–350, 1995.

Hotze, M., et al., *C. roseus* mRNA for cinnamate 4–hydroxylase (CYP73), *EMBL Sequence Database,* Rel. 39, Apr. 15, 1994, Accession No. Z32563, (XP–002054206).

Mizutani, M. et al., Molecular Cloning and Sequencing of a cDNA Encoding Mung Bean Cytochrome P450 Possessing Cinnamate 4–Hydroxylase Activity, *Biochemical and Biophysical Research Communications* 190:3, 875–880, 1993.

Kawai, S., et al., *Populus kitakamiensis* cyp73a gene for cinnamic acid 4–hydroxylase complete cds. *EMBL Sequence Database,* Rel. 46, Dec. 30, 1995, Accession No. D82812 (XP002054135).

Sewalt et al., Reduced Lignin Content and Altered Lignin Composition in Transgenic Tobacco Down–Regulated in Expression of L–Phenylalanine Ammonia–Lyase or Cinnamate 4–Hydroxylase, *Plant Physiol.* 115:41–50, 1997.

Boudet, A.M., et al., Tansley Review No. 80 Biochemistry and molecular biology of lignification, *New Phytoolgist* 129: 203–236, 1995.

Boudet, A.M. et al., Lignin genetic engineering, *Molecular Breeding* 2: 25–39, 1996.

Shiokawa, T., et al., Expression analysis of a cinnamic acid 4–hydroxylase gene from a hybrid aspen, *Populus kitakamiensis,* Chemical Abstracts 125:13, 1996.

Poeydomenge, O., et al., A cDNA Encoding S–Adenosyl–L–Methionine:Caffeic Acid 3–O–Methyl–transferase from Eucalyptus, *Plant Physiol* 105:749–750, 1994.

Mason, M.E., et al., *Pinus elliottii* PEC18 mRNA, partial sequence, *EMBL Sequence Database,* Rel. 47 May 31, 1996, Accession No. U55006 (XP 002054138).

Wagner, A., et al., *Pinus radiata* cinnamyl alcohol dehydrogenase (CAD) mRNA, complete cds, *EMBL Sequence Database*, Rel. 48 Jul. 28, 1996, Accession No. U62394 (XP002054137).

Van Doorsselaere, J., et al., A novel lignin in poplar trees with a reduced caffeic acid/5–hydroxyferulic acid O–methyltransferase activity, *Plant Journal 8*:6, 855–864, 1995.

Ni, Weiting et al., Reduced lignin in transgenic plants containing a caffeic acid O=methyltransferase antisense gene, *Transgenic Research 3*:120–126, 1994.

Halpin, C. et al., Manipulation of lignin quality by down–regulation of cinnamyl alcohol dehydrogenase, *Plant Journal 6*:3, 339–350, 1994.

Leonard Nathan Bloksberg, Studies on the Biology of Phenylalanine Ammonia Lyase and Plant Pathogen Interaction, *Genetics*, Abstract iii, Dec. 1991.

D. Palitha Dharmawardhana et al., A β–Glucosidase from Lodgepole Pine Xylem Specific for the Lignin Precursor Coniferin, *Plant Physiol*, 107:331–339, 1995.

G. Schmid et al., Enzymic synthesis of lignin precursors. Purification and properties of UDP glucose: coniferyl–alcohol glucosyltransferase from cambial sap of spruce (*Picea abies* L.), *Eur J. Biochem 123*: 363–70, 1982.

U. N. Dwivedi et al., Modification of lignin biosynthesis in transgenic Nicotiana through expression of an antisense O–methyltransferase gene from Populus, *Plant Molecular Biology 26*: 61–71, 1994.

Carolyn Napoli et al., Introduction of a Chimeric Chalcone Synthase Gene into Petunia Results in Reversible Co–Suppression of Homologous Genes in trans, *The Plant Cell 2*: 279–289, Apr. 1990.

Ross Whetten et al., Lignin Biosynthesis, *The Plant Cell 7*: 1001–1013, Jul. 1995.

J. Prima–Pettenati et al., Molecular cloning and expression of a *Eucalyptus gunnii* cDNA clone encoding cinnamyl alcohol dehydrogenase, *Plant Mol Biol 21*: 1085–95, 1993.

C. Feuillet et al., Tissue– and cell–specific expression of cinnamyl alcohol dehydrogenase promoter in transgenic poplar plants, *Plant Mol Biol 27*: 651–667, 1995.

H. Wengenmayer et al., Enzymic synthesis of lignin precursors. Purification and properties of a cinnamoyl–CoA: NADPH reductase from cell suspension cultures of soybean (Glycinemax), *Eur J. Biochem* 65:529–536, 1976.

T. Ludertiz et al., Enzymic synthesis of lignin precursors. Comparison of cinnamoyl–CoA reductase and cinnamyl alcohol: NADP+ dehydrogenase from spruce S(*Picea abies* L.) and soybean (*Glycine max* L.), *Eur J. Biochem 119*: 115–124, 1981.

F. Sarni et al., Purification and properties of cinnamoyl–CoA reductase and cinnamyl alcohol dehydrogenase from poplar stems (*Populus X euramericana*) *Eur J. Biochem 139*: 259–265, 1984.

R.C. Bugos, et al., Characterization of bispecific caffeic acid/5–hydroxyferulic acid O–methyltransferase from aspen, *Phytochemistry 31*: 1495–1498, 1992.

C. Hermann et al., Enzymatic synthesis of lignin: purification to homogeneity of the three O–methyltransferases of tobacco and production of specific antibodies, *Arch Biochem Biophys 253*: 367–376, 1987.

J. Van Doorsselaere et al., One–step purification and characterization of a lignin–specific O–methyltransferase from poplar, *Gene 133*: 213–317, 1993.

R.C. Bugos et al., cDNA cloning, sequence analysis and seasonal expression of lignin–bispecific caffeic acid/5–hydroxyferulic acid O–methyltransferase of aspen, *Plant Mol Biol 17*: 1203–1215, 1991.

P. Collazo et al., Structure and expression of the lignin O–methyltransferase gene from *Zea mays* L., *Plant Mol Biol 20*: 857–867, 1992.

W. Hosel et al., Characterization of beta–glucosidase isoenzymes possibly involved in lignification from chick pea (*Cicer arietinum* L.) cell suspension cultures, *Eur J Biochem 84*: 487–492, 1978.

* cited by examiner

MATERIALS AND METHODS FOR THE MODIFICATION OF PLANT LIGNIN CONTENT

REFERENCE TO RELATED APPLICATION

This application is a continuation-in-part application of U.S. patent application Ser. No. 08/713,000 filed Sep. 11, 1996 now U.S. Pat. No. 5,850,020.

TECHNICAL FIELD OF THE INVENTION

This invention relates to the field of modification of lignin content and composition in plants. More particularly, this invention relates to enzymes involved in the lignin biosynthetic pathway and nucleotide sequences encoding such enzymes.

BACKGROUND OF THE INVENTION

Lignin is an insoluble polymer which is primarily responsible for the rigidity of plant stems. Specifically, lignin serves as a matrix around the polysaccharide components of some plant cell walls. The higher the lignin content, the more rigid the plant. For example, tree species synthesize large quantities of lignin, with lignin constituting between 20% to 30% of the dry weight of wood. In addition to providing rigidity, lignin aids in water transport within plants by rendering cell walls hydrophobic and water impermeable. Lignin also plays a role in disease resistance of plants by impeding the penetration and propagation of pathogenic agents.

The high concentration of lignin in trees presents a significant problem in the paper industry wherein considerable resources must be employed to separate lignin from the cellulose fiber needed for the production of paper. Methods typically employed for the removal of lignin are highly energy- and chemical-intensive, resulting in increased costs and increased levels of undesirable waste products. In the U.S. alone, about 20 million tons of lignin are removed from wood per year.

Lignin is largely responsible for the digestibility, or lack thereof, of forage crops, with small increases in plant lignin content resulting in relatively high decreases in digestibility. For example, crops with reduced lignin content provide more efficient forage for cattle, with the yield of milk and meat being higher relative to the amount of forage crop consumed. During normal plant growth, the increase in dry matter content is accompanied by a corresponding decrease in digestibility. When deciding on the optimum time to harvest forage crops, farmers must therefore chose between a high yield of less digestible material and a lower yield of more digestible material.

For some applications, an increase in lignin content is desirable since increasing the lignin content of a plant would lead to increased mechanical strength of wood, changes in its color and increased resistance to rot. Mycorrhizal species composition and abundance may also be favorably manipulated by modifying lignin content and structural composition.

As discussed in detail below, lignin is formed by polymerization of at least three different monolignols which are synthesized in a multistep pathway, each step in the pathway being catalyzed by a different enzyme. It has been shown that manipulation of the number of copies of genes encoding certain enzymes, such as cinnamyl alcohol dehydrogenase (CAD) and caffeic acid 3-O-methyltransferase (COMT) results in modification of the amount of lignin produced; see, for example, U.S. Pat. No. 5,451,514 and PCT publication no. WO 94/23044. Furthermore, it has been shown that antisense expression of sequences encoding CAD in poplar leads to the production of lignin having a modified composition (Grand, C. et al. *Planta* (*Berl.*) 163:232–237 (1985)).

While DNA sequences encoding some of the enzymes involved in the lignin biosynthetic pathway have been isolated for certain species of plants, genes encoding many of the enzymes in a wide range of plant species have not yet been identified. Thus there remains a need in the art for materials useful in the modification of lignin content and composition in plants and for methods for their use.

SUMMARY OF THE INVENTION

Briefly, the present invention provides isolated DNA sequences obtainable from eucalyptus and pine which encode, or partially enccode enzymes involved in the lignin biosynthetic pathway, DNA constructs including such sequences, and methods for the use of such constructs. Transgenic plants having altered lignin content and composition are also provided.

In a first aspect, the present invention provides isolated polynucleotide coding for cinnamyl alcohol dehydrogenase (CAD) isolated from eucalyptus, and for the following enzymes isolated from pine: cinnamate 4-hydroxylase (C4H), coumarate 3-hydroxylase (C3H), phenolase (PNL), 0-methyl transferase (OMT), cinnamyl alcohol dehydrogenase (CAD), cinnamoyl-CoA reductase (CCR), phenylalanine ammonia-lyase (PAL), 4-coumarate:CoA ligase (4CL) and peroxidase (POX). In one embodiment, the isolated polynucleotides comprise a nucleotide sequence selected from the group consisting of: (a) sequences recited in SEQ ID NO: 1–13 and specified portions of the sequences recited in SEQ ID NOS: 2, 4–10, and 12; (b) complements of the sequences recited in SEQ IID NO: 1–13 and complements of specified portions of the sequences recited in SEQ ID NOS: 2, 4–10 and 12; (c) reverse complements of the sequences recited in SEQ ID NO: 1–13 and reverse complements of specified portions of the sequences recited in SEQ ID NOS: 2, 4–10 and 12; (d) reverse sequences of the sequences recited in SEQ ID NO: 1–13 and reverse complements of specified portions of the sequences recited in SEQ ID NOS: 2, 4–10 and 12; and (e) variants of the sequences of (a)–(d).

In another aspect, the invention provides DNA constructs comprising a DNA sequence of the present invention, either alone or in combination with one or more of the inventive sequences, or in combination with one or more known DNA sequences, together with transgenic cells comprising such constructs.

In a related aspect, the present invention provides DNA constructs comprising, in the 5'-3' direction, a gene promoter sequence; a polynucleotide including a sequence disclosed herein, the polynucleotide preferably comprising an open reading frame coding for at least a functional portion of an enzyme involved in a lignin biosynthetic pathway; and a gene termination sequence. The open reading frame may be orientated in either a sense or antisense direction. DNA constructs comprising a polynucleotide including a sequence disclosed herein, the polynucleotide preferably comprising a non-coding region of a gene coding for an enzyme involved in a lignin biosynthetic pathway, together with a gene promoter sequence and a gene termination sequence, are also provided. Preferably, the gene promoter and termination sequences are functional in a host plant. Most preferably, the gene promoter and termination sequences are those of the original enzyme genes but others generally used in the art, such as the Cauliflower Mosaic Virus (CMV) promoter, with or without enhancers, such as the Kozak sequence or Omega enhancer, and *Agrobacterium tumefaciens* nopalin synthase terminator may be usefully employed in the present invention. Tissue-specific promoters may be employed in order to target expression to one or more desired tissues. In a preferred embodiment, the gene promoter sequence provides for transcription in xylem. The DNA construct may further include a marker for the identification of transformed cells.

In a further aspect, transgenic plant cells comprising the DNA constructs of the present invention are provided, together with plants comprising such transgenic cells, and fruits and seeds of such plants.

In yet another aspect, methods for modulating the lignin content and composition of a plant are provided, such methods including stably incorporating into the genome of the plant a DNA construct of the present invention. In a preferred embodiment, the target plant is a woody plant, preferably selected from the group consisting of eucalyptus and pine species, most preferably from the group consisting of *Eucalyptus grandis* and *Pinus radiata*. In a related aspect, a method for producing a plant having altered lignin content is provided, the method comprising transforming a plant cell with a DNA construct of the present invention to provide a transgenic cell, and cultivating the transgenic cell under conditions conducive to regeneration and mature plant growth.

In yet a further aspect, the present invention provides methods for modifying the activity of an enzyme in a plant, comprising stably incorporating into the genome of the plant a DNA construct of the present invention. In a preferred embodiment, the target plant is a woody plant, preferably selected from the group consisting of eucalyptus and pine species, most preferably from the group consisting of *Eucalyptus grandis* and *Pinus radiata*.

The above-mentioned and additional features of the present invention and the manner of obtaining them will become apparent, and the invention will be best understood by reference to the following more detailed description, read in conjunction with the accompanying drawing.

DETAILED DESCRIPTION

Figure 1:
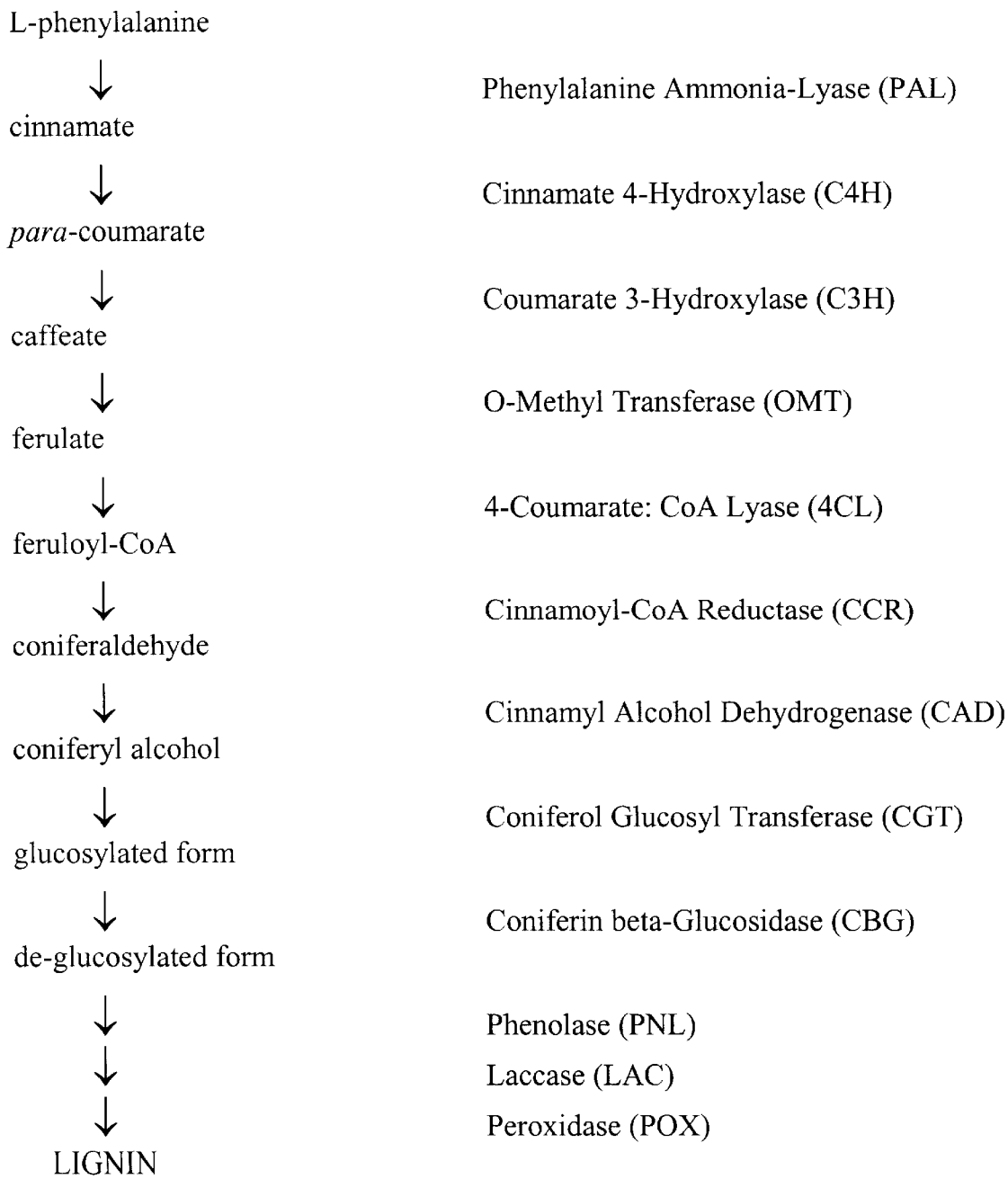
FIG. 1 is a schematic overview of the lignin biosynthetic pathway.

Lignin is formed by polymerization of at least three different monolignols, primarily para-coumaryl alcohol, coniferyl alcohol and sinapyl alcohol. While these three types of lignin subunits are well known, it is possible that slightly different variants of these subunits may be involved in the lignin biosynthetic pathway in various plants. The relative concentration of these residues in lignin varies between different plant species and within species. In addition, the composition of lignin may also vary between different tissues within a specific plant. The three monolignols are derived from phenylalanine in a multistep process and are believed to be polymerized into lignin by a free radical mechanism.

FIG. 1 shows the different steps in the biosynthetic pathway for coniferyl alcohol together with the enzymes responsible for catalyzing each step. para-Coumaryl alcohol and sinapyl alcohol are synthesized by similar pathways. Phenylalanine is first deaminated by phenylalanine ammonia-lyase (PAL) to give cinnamate which is then hydroxylated by cinnamate 4-hydroxylase (C4H) to form p-coumarate. p-Coumarate is hydroxylated by coumarate 3-hydroxylase to give caffeate. The newly added hydroxyl group is then methylated by O-methyl transferase (OMT) to give ferulate which is conjugated to coenzyme A by 4-coumarate:CoA ligase (4CL) to form feruloyl-CoA. Reduction of feruloyl-CoA to coniferaldehyde is catalyzed by cinnamoyl-CoA reductase (CCR). Coniferaldehyde is further reduced by the action of cinnamyl alcohol dehydrogenase (CAD) to give coniferyl alcohol which is then converted into its glucosylated form for export from the cytoplasm to the cell wall by coniferol glucosyl transferase (CGT). Following export, the de-glucosylated form of coniferyl alcohol is obtained by the action of coniferin beta-glucosidase (CBG). Finally, polymerization of the three monolignols to provide lignin is catalyzed by phenolase (PNL), laccase (LAC) and peroxidase (POX). For a more detailed review of the lignin biosynthetic pathway, see: Whetton, R. and Sederoff, R., *The Plant Cell,* 7:1001–1013 (1995).

Quantitative and qualitative modifications in plant lignin content are known to be induced by external factors such as light stimulation, low calcium levels and mechanical stress. Synthesis of new types of lignins, sometimes in tissues not normally lignified, can also be induced by infection with pathogens. In addition to lignin, several other classes of plant products are derived from phenylalanine, including flavonoids, coumarins, stilbenes and benzoic acid derivatives, with the initial steps in the synthesis of all these compounds being the same. Thus modification of the action of PAL, C4H and 4CL may affect the synthesis of other plant products in addition to lignin.

Using the methods and materials of the present invention, the lignin content of a plant can be increased by incorporating additional copies of genes encoding enzymes involved in the lignin biosynthetic pathway into the genome of the target plant. Similarly, a decrease in lignin content can be obtained by transforming the target plant with antisense copies of such genes. In addition, the number of copies of genes encoding for different enzymes in the lignin biosynthetic pathway can be manipulated to modify the relative amount of each monolignol synthesized, thereby leading to the formation of lignin having altered composition. The alteration of lignin composition would be advantageous, for example, in tree processing for paper, and may also be effective in altering the palatability of wood materials to rotting fungi.

In one embodiment, the present invention provides isolated complete or partial DNA sequences encoding, or partially encoding, enzymes involved in the lignin biosynthetic pathway, the DNA sequences being obtainable from eucalyptus and pine. Specifically, the present invention provides isolated DNA sequences encoding the enzyme CAD from *Eucalyptus grandis* (SEQ ID NO: 1) and the enzymes C4H (SEQ ID NO: 2 and 3), C3H (SEQ ID NO: 4), PNL (SEQ ID NO: 5), OMT (SEQ ID NO: 6), CAD (SEQ ID NO: 7), CCR (SEQ ID NO: 8), PAL (SEQ ID NO: 9–11) and 4CL (SEQ ID NO: 12) and POX (SEQ ID NO: 13) from *Pinus radiata*, complements of such isolated DNA sequences, reverse complements of such isolated DNA sequences and reverse sequences of such isolated DNA sequences, together with variants of such sequences. DNA sequences encompassed by the present invention include cDNA, genomic DNA, recombinant DNA, corresponding RNA molecules, and wholly or partially chemically synthesized DNA molecules.

In another embodiment, the present invention provides additional isolated polynucleotides encoding the enzymes C4H (residues 46–671 of SEQ ID NO: 2) C3H (residues 290–949 of SEQ ID NO: 4), PNL (residues 15–959 of SEQ ID NO: 5), OMT (residues 15–1026 of SEQ ID NO: 6), CAD (residues 15–1454 of SEQ ID NO: 7), CCR (residues 15–740 of SEQ ID NO: 8), PAL (residues 108–624 of SEQ ID NO: 9 and residues 68–274 of SEQ ID NO: 10) and 4CL (residues 1–384 of SEQ ID NO: 12) from Pinus radiata, complements of such isolated polynucleotides, reverse complements of such isolated polynucleotides, and reverse sequences of such isolated polynucleotides, together with variants of such sequences. DNA sequences and polynucleotides encompassed by the present invention include cDNA, genomic DNA, recombinant DNA, corresponding RNA molecules, and wholly or partially chemically synthesized DNA molecules.

The definitions of the terms "complement", "reverse complement" and "reverse sequence", as used herein, are best illustrated by the following example. For the sequence 5' AGGACC 3', the complement, reverse complement and reverse sequence are as follows:

complement 3' TCCTGG 5'
reverse complement 3' GGTCCT 5'
reverse sequence 5' CCAGGA 3'.

As used herein, the term "variant" comprehends polynucleotides comprising sequences that hybridize to a polynucleotide of the present invention under stringent hybridization conditions. As used herein, "stringent conditions" mean prewashing in a solution of 6× SSC, 0.2% SDS; hybridizing at 65° C., 6× SSC, 0.2% SDS overnight; followed by two washes of 30 minutes each in 1× SSC, 0.1% SDS at 65° C. and two washes of 30 minutes each in 0.2× SSC, 0.1% SDS at 65° C.

According to another embodiment, the term "variant" comprehends polynucleotides comprising sequences that differ from sequences disclosed herein only in that one or more conservative deletions, insertions, or substitutions have been made. The conservative deletions, insertions, and substitutions preferably affect less than 10% of the total number of sequences comprising the polynucleotide and do not substantially effect the function of a polypeptide encoded by the polynucleotide, the expressed polypeptide having enzymatic activity in a lignin biosynthetic pathway.

According to yet another embodiment, the term "variant" comprehends polynucleotides comprising sequences having 60% similarity, preferably 75% similarity, and more preferably 90% similarity to the sequences disclosed herein, the sequence alignments and similarities determined as described below. Polynucleotide sequence alignments are performed using the BLASTN algorithm version 2.0.4 (Feb. 24, 1998). The use of BLAST family of algorithms, including BLASTN, is described at NCBI's website at URL http://www.ncbi.nlm.nih.gov/BLAST/newblast.html and in the publication of Altshul, Stephen F., et al (1997), "Gapped BLAST and PSI-BLAST: a new generation of protein database search programs", *Nucleic Acids Res.* 25:3389–3402. The following running parameters are preferred for determination of alignments and similarities using BLASTN: Unix running command with default parameter values thus: blastall -p blastn -d embldb -e 10 -G 1 -E 1 -r 2 -v 50 -b 50 -i queryseq -o results.

The percentage similarity is determined by aligning sequences using the BLASTN algorithm as described above; identifying the number of identical nucleic acids over aligned portions; dividing the number of identical nucleic acids by the total number of nucleic acids of the polynucleotide of the present invention; and then multiplying by 100 to determine the percentage similarity. For example, if a 220 nucleic acid polynucleotide of the present invention has a "hit" over a region of 23 nucleotides in the alignment produced by the BLASTN algorithm to a polynucleotide sequence in the EMBL database having 520 nucleic acids, where the similar region includes 21 identical nucleotides, one gap and one different nucleotide, the database "hit" has a percentage similarity to the polynucleotide of the present invention of 21/220 times 100, or 9.5%. The polynucleotide sequence in the EMBL database is thus not a variant of the polynucleotide of the present invention.

Polynucleotides of the present invention also comprehend polynucleotides comprising at least a specified number of contiguous residues (x-mers) of any of the polynucleotides disclosed herein. According to preferred embodiments, the value of x is preferably at least 20, more preferably at least 40, more preferably yet at least 60, and most preferably at least 80. Thus polynucleotides of the present invention include polynucleotides comprising 20-mer, a 40-mer, a 60-mer, an 80-mer, a 100-mer, a 120-mer, a 150-mer, a 180-mer, a 220-mer, a 250-mer, or a 300-mer, 400-mer, 500-mer, or 600-mer of a polynucleotide disclosed herein.

The inventive DNA sequences may be isolated by high throughput sequencing of cDNA libraries prepared from *Eucalyptus grandis* and *Pinus radiata* as described below in Examples 1 and 2. Alternatively, oligonucleotide probes based on the sequences enclosed herein can be synthesized and used to identify positive clones in either cDNA or genomic DNA libraries from *Eucalyptus grandis* and *Pinus radiata* by means of hybridization or PCR techniques. Probes can be shorter than the sequences provided herein but should be at least about 10, preferably at least about 15 and most preferably at least about 20 nucleotides in length. Hybridization and PCR techniques suitable for use with such oligonucleotide probes are well known in the art. Positive clones may be analyzed by restriction enzyme digestion, DNA sequencing or the like.

In addition, the DNA sequences of the present invention may be generated by synthetic means using techniques well known in the art. Equipment for automated synthesis of oligonucleotides is commercially available from suppliers such as Applied Biosystems, Inc. (Foster City, Calif.) and may be operated according to the manufacturer's instructions.

In one embodiment, the DNA constructs of the present invention include an open reading frame coding for at least a functional portion of an enzyme encoded by a nucleotide sequence of the present invention or a variant thereof. As used herein, the "functional portion" of an enzyme is that portion which contains the active site essential for affecting the metabolic step, i.e. the portion of the molecule that is capable of binding one or more reactants or is capable of improving or regulating the rate of reaction. The active site may be made up of separate portions present on one or more polypeptide chains and will generally exhibit high substrate specificity. The term "enzyme encoded by a nucleotide sequence" as used herein, includes enzymes encoded by a nucleotide sequence which includes the partial isolated DNA sequences of the present invention.

For applications where amplification of lignin synthesis is desired, the open reading frame is inserted in the DNA construct in a sense orientation, such that transformation of a target plant with the DNA construct will lead to an increase in the number of copies of the gene and therefore an increase in the amount of enzyme. When down-regulation of lignin synthesis is desired, the open reading frame is inserted in the DNA construct in an antisense orientation, such that the RNA produced by transcription of the DNA sequence is complementary to the endogenous mRNA sequence. This, in turn, will result in a decrease in the number of copies of the gene and therefore a decrease in the amount of enzyme. Alternatively, regulation can be achieved by inserting appropriate sequences or subsequences (e.g. DNA or RNA) in ribozyme constructs.

In a second embodiment, the inventive DNA constructs comprise a nucleotide sequence including a non-coding region of a gene coding for an enzyme encoded by a DNA sequence of the present invention, or a nucleotide sequence complementary to such a non-coding region. Examples of non-coding regions which may be usefully employed in such constructs include introns and 5'-non-coding leader sequences. Transformation of a target plant with such a DNA construct may lead to a reduction in the amount of lignin synthesized by the plant by the process of cosuppression, in a manner similar to that discussed, for example, by Napoli et al. (*Plant Cell* 2:279–290, 1990) and de Carvalho Niebel et al. (*Plant Cell* 7:347–358, 1995).

The DNA constructs of the present invention further comprise a gene promoter sequence and a gene termination sequence, operably linked to the DNA sequence to be transcribed, which control expression of the gene. The gene promoter sequence is generally positioned at the 5' end of the DNA sequence to be transcribed, and is employed to initiate transcription of the DNA sequence. Gene promoter sequences are generally found in the 5' non-coding region of a gene but they may exist in introns (Luehrsen, K. R., *Mol. Gen. Genet.* 225:81–93, 1991) or in the coding region, as for example in PAL of tomato (Bloksberg, 1991, Studies on the Biology of Phenylalanine ammonia lyase and plant pathogen interaction. Ph.D. Thesis, Univ. of California, Davis, University Microfilms International order number 9217564). When the construct includes an open reading frame in a sense orientation, the gene promoter sequence also initiates translation of the open reading frame. For DNA constructs comprising either an open reading frame in an antisense orientation or a non-coding region, the gene promoter sequence consists only of a transcription initiation site having a RNA polymerase binding site.

A variety of gene promoter sequences which may be usefully employed in the DNA constructs of the present invention are well known in the art. The promoter gene sequence, and also the gene termination sequence, may be endogenous to the target plant host or may be exogenous, provided the promoter is functional in the target host. For example, the promoter and termination sequences may be from other plant species, plant viruses, bacterial plasmids and the like. Preferably, gene promoter and termination sequences are from the inventive sequences themselves.

Factors influencing the choice of promoter include the desired tissue specificity of the construct, and the timing of transcription and translation. For example, constitutive promoters, such as the 35S Cauliflower Mosaic Virus (CaMV 35S) promoter, will affect the activity of the enzyme in all parts of the plant. Use of a tissue specific promoter will result in production of the desired sense or antisense RNA only in the tissue of interest. With DNA constructs employing inducible gene promoter sequences, the rate of RNA polymerase binding and initiation can be modulated by external stimuli, such as light, heat, anaerobic stress, alteration in nutrient conditions and the like. Temporally regulated promoters can be employed to effect modulation of the rate of RNA polymerase binding and initiation at a specific time during development of a transformed cell. Preferably, the original promoters from the enzyme gene in question, or promoters from a specific tissue-targeted gene in the organism to be transformed, such as eucalyptus or pine are used. Other examples of gene promoters which may be usefully employed in the present invention include, mannopine synthase (mas), octopine synthase (ocs) and those reviewed by Chua et al. (*Science*, 244:174–181, 1989).

The gene termination sequence, which is located 3' to the DNA sequence to be transcribed, may come from the same gene as the gene promoter sequence or may be from a different gene. Many gene termination sequences known in the art may be usefully employed in the present invention, such as the 3' end of the *Agrobacterium tumefaciens* nopaline synthase gene. However, preferred gene terminator sequences are those from the original enzyme gene or from the target species to be transformed.

The DNA constructs of the present invention may also contain a selection marker that is effective in plant cells, to allow for the detection of transformed cells containing the inventive construct. Such markers, which are well known in the art, typically confer resistance to one or more toxins. One example of such a marker is the NPTII gene whose expression results in resistance to kanamycin or hygromycin, antibiotics which is usually toxic to plant cells at a moderate concentration (Rogers et al. in *Methods for Plant Molecular Biology*, A. Weissbach and H. Weissbach, eds., Academic Press Inc., San Diego, Calif. (1988)). Alternatively, the presence of the desired construct in transformed cells can be determined by means of other techniques well known in the art, such as Southern and Western blots.

Techniques for operatively linking the components of the inventive DNA constructs are well known in the art and include the use of synthetic linkers containing one or more restriction endonuclease sites as described, for example, by Maniatis et al., (*Molecular Cloning: A Laboratory Manual*, Cold Spring Harbor Laboratories, Cold Spring Harbor, N.Y., 1989). The DNA construct of the present invention may be linked to a vector having at least one replication system, for example, *E. coli*, whereby after each manipulation, the resulting construct can be cloned and sequenced and the correctness of the manipulation determined.

The DNA constructs of the present invention may be used to transform a variety of plants, both monocotyledonous (e.g. grasses, corn, grains, oat, wheat and barley), dicotyledonous (e.g. Arabidopsis, tobacco, legumes, alfalfa, oaks, eucalyptus, maple), and Gymnosperms (e.g. Scots pine (Aronen, Finnish Forest Res. Papers, vol. 595, 1996), white spruce (Ellis et al., *Biotechnology* 11:94–92, 1993), larch (Huang et al., In Vitro *Cell* 27:201–207, 1991). In a preferred embodiment, the inventive DNA constructs are employed to transform woody plants, herein defined as a tree or shrub whose stem lives for a number of years and increases in diameter each year by the addition of woody tissue. Preferably the target plant is selected from the group consisting of eucalyptus and pine species, most preferably from the group consisting of *Eucalyptus grandis* and *Pinus radiata*. As discussed above, transformation of a plant with a DNA construct including an open reading frame coding for an enzyme encoded by an inventive DNA sequence wherein the open reading frame is orientated in a sense direction will lead to an increase in lignin content of the plant or, in some cases, to a decrease by cosuppression. Transformation of a plant with a DNA construct comprising an open reading frame in an antisense orientation or a non-coding (untranslated) region of a gene will lead to a decrease in the lignin content of the transformed plant.

Techniques for stably incorporating DNA constructs into the genome of target plants are well known in the art and include *Agrobacterium tumefaciens* mediated introduction, electroporation, protoplast fusion, injection into reproductive organs, injection into immature embryos, high velocity projectile introduction and the like. The choice of technique will depend upon the target plant to be transformed. For example, dicotyledonous plants and certain monocots and gymnosperms may be transformed by Agrobacterium Ti plasmid technology, as described, for example by Bevan (*Nucl. Acid Res.* 12:8711–8721, 1984). Targets for the introduction of the DNA constructs of the present invention include tissues, such as leaf tissue, disseminated cells, protoplasts, seeds, embryos, meristematic regions; cotyledons, hypocotyls, and the like. The preferred method for transforming eucalyptus and pine is a biolistic method using pollen (see, for example, Aronen 1996, Finish Forest Res. Papers vol. 595, 53pp) or easily regenerable embryonic tissues.

Once the cells are transformed, cells having the inventive DNA construct incorporated in their genome may be selected by means of a marker, such as the kanamycin resistance marker discussed above. Transgenic cells may then be cultured in an appropriate medium to regenerate whole plants, using techniques well known in the art. In the case of protoplasts, the cell wall is allowed to reform under appropriate osmotic conditions. In the case of seeds or embryos, an appropriate germination or callus initiation medium is employed. For explants, an appropriate regeneration medium is used. Regeneration of plants is well established for many species. For a review of regeneration of forest trees see Dunstan et al., Somatic embryogenesis in woody plants. In: Thorpe, T. A. ed., 1995: in vitro embryogenesis of plants. Vol. 20 in Current Plant Science and Biotechnology in Agriculture, Chapter 12, pp. 471–540. Specific protocols for the regeneration of spruce are discussed by Roberts et al., (Somatic Embryogenesis of Spruce. In: *Synseed. Applications of synthetic seed to crop improvement*. Redenbaugh, K., ed. CRC Press, Chapter 23, pp. 427–449, 1993). The resulting transformed plants may be reproduced sexually or asexually, using methods well known in the art, to give successive generations of transgenic plants. The present invention therefore encompasses plants incorporating a transgenic plant cell comprising a polynucleotide of the present invention, as well as fruit, seeds, and progeny of such plants or transgenic plant cells.

As discussed above, the production of RNA in target plant cells can be controlled by choice of the promoter sequence, or by selecting the number of functional copies or the site of integration of the DNA sequences incorporated into the genome of the target plant host. A target plant may be transformed with more than one DNA construct of the present invention, thereby modulating the lignin biosynthetic pathway for the activity of more than one enzyme, affecting enzyme activity in more than one tissue or affecting enzyme activity at more than one expression time. Similarly, a DNA construct may be assembled containing more than one open reading frame coding for an enzyme encoded by a DNA sequence of the present invention or more than one non-coding region of a gene coding for such an enzyme. The DNA sequences of the present inventive may also be employed in combination with other known sequences encoding enzymes involved in the lignin biosynthetic pathway. In this manner, it may be possible to add a lignin biosynthetic pathway to a non-woody plant to produce a new woody plant.

The isolated DNA sequences of the present invention may also be employed as probes to isolate DNA sequences encoding enzymes involved in the lignin synthetic pathway from other plant species, using techniques well known to those of skill in the art.

The following examples are offered by way of illustration and not by way of limitation.

EXAMPLE 1

Isolation and Characterization of cDNA Clones from *Eucalyptus grandis*

Two *Eucalyptus grandis* cDNA expression libraries (one from a mixture of various tissues from a single tree and one from leaves of a single tree) were constructed and screened as follows.

mRNA was extracted from the plant tissue using the protocol of Chang et al. (*Plant Molecular Biology Reporter* 11:113–116 (1993)) with minor modifications. Specifically, samples were dissolved in CPC-RNAXB (100 mM Tris-Cl, pH 8,0; 25 mM EDTA; 2.0 M NaCl; 2%CTAB; 2% PVP and 0.05% Spermidine*3 HCl)and extracted with Chloroform:i-soamyl alcohol, 24:1. mRNA was precipitated with ethanol and the total RNA preparate was purified using a Poly(A) Quik mRNA Isolation Kit (Stratagene, La Jolla, Calif.). A cDNA expression library was constructed from the purified mRNA by reverse transcriptase synthesis followed by insertion of the resulting cDNA clones in Lambda ZAP using a ZAP Express cDNA Synthesis Kit (Stratagene), according to the manufacturer's protocol. The resulting cDNAs were packaged using a Gigapack II Packaging Extract (Stratagene) employing 1 µl of sample DNA from the 5 µl ligation mix. Mass excision of the library was done using XL1-Blue MRF' cells and XLOLR cells (Stratagene) with ExAssist helper phage (Stratagene). The excised phagemids were diluted with NZY broth (Gibco BRL, Gaithersburg, Md.) and plated out onto LB-kanamycin agar plates containing X-gal and isopropylthio-beta-galactoside (IPTG).

Of the colonies plated and picked for DNA miniprep, 99% contained an insert suitable for sequencing. Positive colonies were cultured in NZY broth with kanamycin and cDNA was purified by means of alkaline lysis and polyethylene glycol (PEG) precipitation. Agarose gel at 1% was used to screen sequencing templates for chromosomal contamination. Dye primer sequences were prepared using a Turbo Catalyst 800 machine (Perkin Elmer/Applied Biosystems, Foster City, Calif.) according to the manufacturer's protocol.

DNA sequence for positive clones was obtained using an Applied Biosystems Prism 377 sequencer. cDNA clones were sequenced first from both the 5' end and, in some cases, also from the 3' end. For some clones, internal sequence was obtained using subcloned fragments. Subcloning was performed using standard procedures of restriction mapping and subcloning to pBluescript II SK+ vector.

The determined cDNA sequence was compared to known sequences in the EMBL database (release 46, March 1996) using the FASTA algorithm of February 1996 (version 2.0u4) (available on the Internet at the ftp site ftp://ftp.virginia.edu/pub/fasta/). Multiple alignments of redundant sequences were used to build up reliable consensus sequences. Based on similarity to known sequences from other plant species, the isolated DNA sequence (SEQ ID NO: 1) was identified as encoding a CAD enzyme.

EXAMPLE 2

Isolation and Characterization of cDNA Clones from *Pinus radiata* a) Isolation of cDNA clones by high through-put screening

A *Pinus radiata* cDNA expression library was constructed from xylem and screened as described above in Example 1. DNA sequence for positive clones was obtained using forward and reverse primers on an Applied Biosystems Prism 377 sequencer and the determined sequences were compared to known sequences in the database as described above.

Based on similarity to known sequences from other plant species, the isolated DNA sequences were identified as encoding the enzymes C4H (SEQ ID NO: 2 and 3), C3H (SEQ ID NO: 4), PNL (SEQ ID NO: 5), OMT (SEQ ID NO: 6), CAD (SEQ ID NO: 7), CCR (SEQ ID NO: 8), PAL (SEQ ID NO: 9–11) and 4CL (SEQ ID NO: 12).

b) Isolation of cDNA clones by PCR

Two PCR probes, hereinafter referred to as LNB010 and LNB011 (SEQ ID NO: 14 and 15, respectively) were designed based on conserved domains in the following peroxidase sequences previously identified in other species: vanpox, hvupox6, taepox, hvupox1, osapox, ntopox2, ntopox1, lespox, pokpox, luspox, athpox, hrpox, spopox, and tvepox (Genbank accession nos. D11337, M83671, X56011, X58396, X66125, J02979, D11396, X71593, D11102, L07554, M58381, X57564, Z22920, and Z31011, respectively).

RNA was isolated from pine xylem and first strand cDNA was synthesized as described above. This cDNA was subjected to PCR using 4 µM LNB010, 4 µM LNB011, 1× Kogen's buffer, 0.1 mg/ml BSA, 200 mM dNTP, 2 mM $Mg^{2+}$, and 0.1 U/µl of Taq polymerase (Gibco BRL). Conditions were 2 cycles of 2 min at 94° C., 1 min at 55° C. and 1 min at 72° C.; 25 cycles of 1 min at 94° C., 1 min at 55° C., and 1 min at 72° C.; and 18 cycles of 1 min at 94° C., 1 min at 55° C., and 3 min at 72° C. in a Stratagene Robocycler. The gene was re-amplified in the same manner. A band of about 200 bp was purified from a TAE agaorse gel using a Schleicher & Schuell Elu-Quik DNA purification kit and clones into a T-tailed pBluescript vector (Marchuk D. et al., *Nucleic Acids Res.* 19:1154, 1991). Based on similarity to known sequences, the isolated gene (SEQ ID NO: 13) was identified as encoding pine peroxidase (POX).

Although the present invention has been described in some detail by way of illustration and example for purposes of clarity of understanding, changes and modifications can be carried out without departing from the scope of the invention which is intended to be limited only by the scope of the appended claims.

What is claimed is:

1. An isolated polynucleotide comprising a nucleotide sequence selected from the group consisting of:
residues 46–671 of SEQ ID NO: 2; residues 290–949 of SEQ ID NO: 4; residues 15–959 of SEQ ID NO: 5; residues 108–624 of SEQ ID NO: 9; residues 68–274 of SEQ ID NO: 10; and residues 1–384 of SEQ ID NO: 12.

2. An isolated polynucleotide comprising a nucleotide sequence selected from the group consisting of: complements, reverse complements and reverse sequences of a nucleotide sequence selected from the group consisting of: residues 46–671 of SEQ ID NO: 2; residues 290–949 of SEQ ID NO: 4; residues 15–959 of SEQ ID NO: 5; residues 108–624 of SEQ ID NO: 9; residues 68–274 of SEQ ID NO: 10; and residues 1–384 of SEQ ID NO: 12.

3. An isolated polynucleotide comprising a nucleotide sequence that hybridizes under stringent hybridization conditions to a sequence selected from the group consisting of:
   (a) sequences recited in residues 46–671 of SEQ ID NO: 2, residues 290–949 of SEQ ID NO: 4, resides 15–959 of SEQ ID NO: 5, residues 108–624 of SEQ ID NO: 9, residues 68–274 of SEQ ID NO: 10, and residues 1–384 of SEQ ID NO: 12;
   (b) sequences recited in SEQ ID NOS: 1, 3, 11 and 13;
   (c) complements of a sequence of (a) or (b);
   (d) reverse complements of a sequence of (a) or (b); and
   (e) reverse sequences of a sequence of (a) or (b).

4. An isolated polynucleotide comprising a nucleotide sequence that differs only in one or more conservative deletions, insertions or substitutions from a sequence selected from the group consisting of:
   (a) sequences recited in residues 46–671 of SEQ ID NO: 2, residues 290–949 of SEQ ID NO: 4, residues 15–959 of SEQ ID NO: 5, residues 108–624 of SEQ ID NO: 9, residues 68–274 of SEQ ID NO: 10, and residues 1–384 of SEQ ID NO: 12;
   (b) sequences recited in SEQ ID NOS: 1, 3, 11 or 13;
   (c) complements of a sequence of (a) or (b);
   (d) reverse complements of a sequence of (a) or (b); and
   (e) reverse sequences of a sequence of (a) or (b).

5. An isolated polynucleotide comprising a nucleotide sequence having at least 60% similarity to a sequence selected from the group consisting of:
   (a) sequences recited in residues 46–671 of SEQ ID NO: 2, residues 290–949 of SEQ ID NO: 4, residues 15–959 of SEQ ID NO: 5, residues 108–624 of SEQ ID NO: 9, and residues 68–274 of SEQ ID NO: 10;
   (b) sequences recited in SEQ ID NOS: 1, 3, 11 or 13;
   (c) complements of a sequence of (a) or (b);
   (d) reverse complements of a sequence of (a) or (b); and
   (e) reverse sequences of a sequence of (a) or (b);
   the percentage similarity being determined by aligning the sequence and the compare sequence using the BLASTN algorithm Version 2.04 set at the parameters described above in the specification, identifying the number of identical nucleic acids over the aligned regions of the sequence and compare sequence, dividing the number of identical nucleic acids by the total number of nucleic acids in the compare sequence, and multiplying by 100 to determine the percentage similarity.

6. An isolated polynucleotide comprising a nucleotide sequence that is a 40-mer of a sequence selected from the group consisting of:
   (a) sequences recited in residues 46–671 of SEQ ID NO: 2, residues 290–949 of SEQ ID NO: 4, residues 15–959 of SEQ ID NO: 5, residues 108–624 of SEQ ID NO: 9, residues 68–274 of SEQ ID NO: 10, and residues 1–384 of SEQ ID NO: 12;

(b) sequences recited in SEQ ID NOS: 1, 3, 11 or 13;

(c) complements of a sequence of (a) or (b);

(d) reverse complements of a sequence of (a) or (b); and (e) reverse sequences of a sequence of (a) or (b).

7. An isolated polynucleotide comprising a nucleotide sequence selected from the group consisting of:

(a) residues 15–1026 of SEQ ID NO: 6 and residues 15–740 of SEQ ID NO: 8;

(b) complements, reverse complements, and reverse sequences of the sequences recited in (a);

(c) sequences that hybridize to a sequence recited in (a) or (b), above, under stringent hybridization conditions;

(d) sequences that differ from a sequence recited in (a) or (b), above, only in one or more conservative deletions, insertions, or substitutions;

(e) sequences having at least 60% similarity to a compare sequence recited in (a) or (b), above, the percentage similarity being determined by aligning the sequence and the compare sequence using the BLASTN algorithm Version 2.04 set at the parameters described above in the specification, identifying the number of identical nucleic acids over the aligned regions of the sequence and compare sequence, dividing the number of identical nucleic acids by the total number of nucleic acids in the compare sequence, and multiplying by 100 to determine the percentage similarity; and (f) a 40-mer of a sequence recited in (a) or (b), above.

8. A DNA construct comprising a polynucleotide of any one of claims 1, 2, 3, 4, 5, 6 and 7.

9. A transgenic cell comprising a DNA construct according to claim 2.

10. A DNA construct comprising, in the 5′–3′ direction:

(a) a gene promoter sequence;

(b) a polynucleotide of any one of claims 1, 2, 3, 4, 5, 6 and 7 comprising at least one open reading frame coding for at least one functional portion of an enzyme involved in a lignin biosynthetic pathway; and (c) a gene termination sequence.

11. The DNA construct of claim 10 wherein at least one open reading frame is in a sense orientation.

12. The DNA construct of claim 10 wherein at least one open reading frame is in an antisense orientation.

13. The DNA construct of claim 10, wherein the gene promoter sequence and gene termination sequences are functional in a plant host.

14. The DNA construct of claim 10, wherein the gene promoter sequence provides for transcription in xylem.

15. A transgenic plant cell comprising a DNA construct of claim 10.

16. A plant comprising a transgenic plant cell of claim 15, and fruit, seeds, and progeny thereof.

17. A DNA construct comprising, in the 5′–3′ direction:

(a) a gene promoter sequence, (b) a polynucleotide of any one of claims 1, 2, 3, 4, 5, 6 and 7 comprising a non-coding region of a gene coding for an enzyme involved in a lignin biosynthetic pathway; and (c) a gene termination sequence.

18. The DNA construct of claim 17 wherein the non-coding region is in a sense orientation.

19. The DNA construct of claim 17 wherein the non-coding region is in an antisense orientation.

20. The DNA construct of claim 17, wherein the gene promoter sequence and gene termination sequences are functional in a plant host.

21. The DNA construct of claim 17, wherein the gene promoter sequence provides for transcription in xylem.

22. A transgenic plant cell comprising a DNA construct of claim 17.

23. A plant comprising a transgenic plant cell according to claim 17, and fruit, seeds, and progeny thereof.

24. A method for modulating the lignin content of a plant comprising stably incorporating into the genome of the plant a polynucleotide of any one of claims 1, 2, 3, 4, 5, 6 and 7.

25. The method of claim 24 wherein the plant is selected from the group consisting of eucalyptus and pine species.

26. The method of claim 24 comprising stably incorporating into the genome of a plant a DNA construct of claim 10.

27. The method of claim 24 comprising stably incorporating into the genome of a plant a DNA construct of claim 17.

28. A method for producing a plant having altered lignin structure comprising:

(a) transforming a plant cell with a polynucleotide of any one of claims 1, 2, 3, 4, 5, 6 and 7; and (b) cultivating the transgenic cell under conditions conducive to regeneration and mature plant growth.

29. The method of claim 28 comprising stably incorporating into the genome of a plant a DNA construct of claim 10.

30. The method of claim 28 comprising stably incorporating into the genome of a plant a DNA construct of claim 17.

31. A method of modifying the activity of an enzyme in a plant comprising stably incorporating into the genome of the plant a polynucleotide of any one of claims 1, 2, 3, 4, 5, 6 and 7.

32. The method of claim 31 comprising stably incorporating into the genome of a plant a DNA construct of claim 10.

33. The method of claim 31 comprising stably incorporating into the genome of a plant a DNA construct of claim 17.

* * * * *

UNITED STATES PATENT AND TRADEMARK OFFICE
CERTIFICATE OF CORRECTION

PATENT NO. : 6,204,434 B1
DATED : March 20, 2001
INVENTOR(S) : Leonard N. Bloksberg, Ilkka Havukkala, and Alastair Grierson Page 1 of 1

It is certified that error appears in the above-identified patent and that said Letters Patent is hereby corrected as shown below:

<u>Column 24,</u>
Lines 63-64, delete "residues 46-671 of SEQ ID NO: 2,"
Line 65, replace "SEQ ID NO: 9," with -- SEQ ID NO: 9, and --
Lines 66-67, delete ", and residues 1-384 of SEQ ID NO: 12"

Signed and Sealed this

Thirteenth Day of November, 2001

Attest:

NICHOLAS P. GODICI
Attesting Officer
*Acting Director of the United States Patent and Trademark Office*

UNITED STATES PATENT AND TRADEMARK OFFICE
CERTIFICATE OF CORRECTION

PATENT NO.     : 6,204,434 B1
DATED          : March 20, 2001
INVENTOR(S)    : Leonard N. Bloksberg, Ilkka Havukkala and Alastair Grierson It is certified that error appears in the above-identified patent and that said Letters Patent is hereby corrected as shown below:

Column 23,
Line 42, before "complements", please insert -- full-length --
Line 42, before "reverse complements", please insert -- full-length --
Line 42, before "reverse sequences", please insert -- full-length --
Line 49, before "hybridizes", please insert -- fully --
Line 58, before "complements", please insert -- full-length --
Line 59, before "reverse compliments", please insert -- full-length --
Line 60, before "reverse sequences", please insert -- full-length --
Line 60, please delete (e) "reverse sequences of a sequence of (a) or (b)." and replace with -- (e) full-length reverse sequences of a sequence of (a) or (b); --
Line 60, after line 60, please insert -- wherein the coding sequence of said isolated polynucleotide has lignin biosynthetic enzymatic activity. --
Lines 62-63, please delete "sequence that differs only in one or more conservative deletions, insertions or substitutions from a sequence" and replace with -- sequence that differs only in one or more deletions, insertions or conservative substitutions from a sequence --

Column 24,
Line 36, before "complements", please insert, -- full-length --
Line 37, before "reverse complements", please insert, -- full-length --
Line 38, please delete "(e) reverse sequences of a sequence of (a) or (b)." and replace with -- (e) full-length reverse sequences of a sequences of (a) or (b); --
Line 38, after line 38, please insert -- wherein the coding sequence of said isolated polynucleotide has lignin biosynthetic enzymatic activity. --
Line 39, before "nucleotide sequence", please insert -- first --
Line 40, before "sequence", please insert -- second --
Line 46, before "complements", please insert -- full-length --
Line 47, before "reverse complements", please insert -- full-length --
Line 48, before "reverse sequences", please insert -- full-length --
After line 48, please insert -- wherein the coding sequence of said isolated polynucleotide has lignin biosynthetic enzymatic activity and wherein --

UNITED STATES PATENT AND TRADEMARK OFFICE
CERTIFICATE OF CORRECTION

PATENT NO. : 6,204,434 B1
DATED : March 20, 2001
INVENTOR(S) : Leonard N. Bloksberg, Ilkka Havukkala and Alastair Grierson It is certified that error appears in the above-identified patent and that said Letters Patent is hereby corrected as shown below:

Column 24, cont'd,
Line 50, please delete "the percentage similarity being determined by aligning the" and replace with -- the percentage similarity is determined by aligning the first --
Line 51, please delete "sequences and the compare sequence using the" and replace with -- sequences and the second sequence using the --
Lines 55-56, please delete "regions of the sequence and compare sequence, dividing" and replace with -- regions of the first sequence and the second sequence, dividing --
Line 57, please delete "number of nucleic acids in the compare sequence, and" and replace with -- number of nucleic acids in the second sequence, and --

Column 25,
Line 2, before "complements", please insert -- full-length --
Line 3, before "reverse complements", please insert -- full-length --
Line 4, before "reverse sequences", please insert -- full-length --
Lines 10-11, please delete "(b) complements, reverse complements, and reverse sequences of the sequences recited in (a);" and replace with -- (b) full-length complements, full-length reverse complements, and full-length reverse sequences of the sequences recited in (a); --
Line 12, before "hybridize", please insert -- fully --
Lines 15-17, please delete "(d) sequences that differ from a sequence recited in (a) or (b), above, only in one or more conservative deletions, insertions, or substitutions;" and replace with -- (d) sequences that differ from the sequence recited in (a) or (b), above, only in one or more deletions, insertions, or conservative substitutions; --
Line 19, please delete "sequences having at least 60% similarity to a compare" and replace with -- second sequences having at least 60% similarity to a first --
Line 20, please delete "sequence recited in (a) or (b), above, the percentage" and replace with -- first sequence as recited in (a) or (b), above, wherein the percentage --
Line 21, please delete "similarity being determined by aligning the sequence" and replace with -- similarity is determined by aligning the first sequence --

UNITED STATES PATENT AND TRADEMARK OFFICE
CERTIFICATE OF CORRECTION

PATENT NO. : 6,204,434 B1
DATED : March 20, 2001
INVENTOR(S) : Leonard N. Bloksberg, Ilkka Havukkala and Alastair Grierson It is certified that error appears in the above-identified patent and that said Letters Patent is hereby corrected as shown below:

Column 25, cont'd,
Lines 22-23, please delete "and the compare sequence using the BLASTN algorithm" and replace with -- and the second sequence using the BLASTN algorithm --
Line 26, please delete "sequence and compare sequence, dividing the number of" and replace with -- first sequence and the second sequence, dividing the number of --
Line 28, please delete "acids in the compare sequence, and multiplying by 100" and replace with -- acids in the second sequence, and multiplying by 100 --
Line 30, please delete "(f) a 40-mer of a sequence recited in (a) or (b), above." and replace with -- (f) a 40-mer of a sequence recited in (a) or (b), above; --
After line 30, please insert -- wherein the coding sequence of said isolated polynucleotide having the sequences of (a), (b), (c), (d) or (e) has lignin biosynthetic enzymatic activity. --

Signed and Sealed this

Twenty-seventh Day of May, 2003

JAMES E. ROGAN
*Director of the United States Patent and Trademark Office*

SEQUENCE LISTING

<160> NUMBER OF SEQ ID NOS: 15

<210> SEQ ID NO 1
<211> LENGTH: 535
<212> TYPE: DNA
<213> ORGANISM: Eucalyptus grandis
<220> FEATURE:
<221> NAME/KEY: unsure
<222> LOCATION: (110)...(110)

<400> SEQUENCE: 1

```
cttcgcgcta ccgcatactc caccaccgcg tgcagaagat gagctcggag ggtgggaagg      60
aggattgcct cggttgggct gcccgggacc cttctggttt cctctccccn tacaaattca     120
cccgcaggcc gtgggaagcg aagacgtctc gattaagatc acgcactgtg gagtgtgcta     180
cgcagatgtg gcttggacta ggaatgtgca gggacactcc aagtatcctc tggtgccggg     240
gcacgagata gttggaattg tgaaacaggt tggctccagt gtccaacgct tcaaagttgg     300
cgatcatgtg ggggtgggaa cttatgtcaa ttcatgcaga gagtgcgagt attgcaatga     360
caggctagaa gtccaatgtg aaaagtcggt tatgactttt gatggaattg atgcagatgg     420
tacagtgaca aagggaggat attctagtca cattgtcgtc catgaaaggt attgcgtcag     480
gattccagaa aactacccga tggatctagc agcgcattgc tctgtgctgg atcac         535
```

<210> SEQ ID NO 2
<211> LENGTH: 671
<212> TYPE: DNA
<213> ORGANISM: Pinus radiata

<400> SEQUENCE: 2

```
gcgcctgcag gtcgacacta gtggatccaa agaattcggc acgaggttgc aggtcgggga      60
tgatttgaat cacagaaacc tcagcgattt tgccaagaaa tatggcaaaa tctttctgct     120
caagatgggc cagaggaatc ttgtggtagt ttcatctccc gatctcgcca aggaggtcct     180
```

-continued

| | |
|---|---|
| gcacacccag ggcgtcgagt ttgggtctcg aacccggaac gtggtgttcg atatcttcac | 240 |
| gggcaagggg caggacatgg tgttcaccgt ctatggagat cactggagaa agatgcgcag | 300 |
| gatcatgact gtgcctttct ttacgaataa agttgtccag cactacagat tcgcgtggga | 360 |
| agacgagatc agccgcgtgg tcgcggatgt gaaatcccgc gccgagtctt ccacctcggg | 420 |
| cattgtcatc cgtagcgcct ccagctcatg atgtataata ttatgtatag gatgatgttc | 480 |
| gacaggagat tcgaatccga ggacgacccg ctttcctca agctcaaggc cctcaacgga | 540 |
| gagcgaagtc gattggccca gagctttgag tacaattatg gggatttcat tcccagtctt | 600 |
| aggcccttcc tcagaggtta tcacagaatc tgcaatgaga ttaaagagaa acggctctct | 660 |
| cttttcaagg a | 671 |

<210> SEQ ID NO 3
<211> LENGTH: 940
<212> TYPE: DNA
<213> ORGANISM: Pinus radiata
<220> FEATURE:
<221> NAME/KEY: unsure
<222> LOCATION: (463)...(463)

<400> SEQUENCE: 3

| | |
|---|---|
| cttcaggaca agggagagat caatgaggat aatgttttgt acatcgttga gaacatcaac | 60 |
| gttgcagcaa ttgagacaac gctgtggtcg atggaatggg gaatagcgga gctggtgaac | 120 |
| caccaggaca ttcagagcaa ggtgcgcgca gagctggacg ctgttcttgg accaggcgtg | 180 |
| cagataacgg aaccagacac gacaaggttg ccctaccttc aggcggttgt gaaggaaacc | 240 |
| cttcgtctcc gcatggcgat cccgttgctc gtcccccaca tgaatctcca cgacgccaag | 300 |
| ctcgggggct acgatattcc ggcagagagc aagatcctgg tgaacgcctg gtggttggcc | 360 |
| aacaaccccg ccaactggaa gaaccccgag gagttccgcc cgagcggtt cttcgaggag | 420 |
| gagaagcaca ccgaagccaa tggcaacgac ttcaaattcc tgnccttcgg tgtggggagg | 480 |
| aggagctgcc cgggaatcat tctggcgctg ctctcctcgc actctccatc ggaagacttg | 540 |
| ttcagaactt ccaccttctg ccgccgcccg ggcagagcaa agtggatgtc actgagaagg | 600 |
| gcgggcaatt cagccttcac attctcaacc attctctcat cgtcgccaag cccatagctt | 660 |
| ctgcttaatc ccaacttgtc agtgactggt atataaatgc gcgcacctga acaaaaaaca | 720 |
| ctccatctat catgactgtg tgtgcgtgtc cactgtcgag tctactaaga gctcatagca | 780 |
| cttcaaaagt ttgctaggat ttcaataaca gacaccgtca attatgtcat gtttcaataa | 840 |
| aagtttgcat aaattaaatg atatttcaat atactatttt gactctccac caattgggga | 900 |
| attttactgc taaaaaaaaa aaaaaaaaa aaaaaaaaa | 940 |

<210> SEQ ID NO 4
<211> LENGTH: 949
<212> TYPE: DNA
<213> ORGANISM: Pinus radiata
<220> FEATURE:
<221> NAME/KEY: unsure
<222> LOCATION: (1)...(949)
<223> OTHER INFORMATION: n at all occurrences indicates unsure

<400> SEQUENCE: 4

| | |
|---|---|
| nngctcnacc gacggtggac ggtccgctac tcagtaactg agtgggatcc cccgggctga | 60 |
| caggcaattc gatttagctc actcattagg cacccccaggc tttacacttt atgcttccgg | 120 |
| ctcgtatgtt gtgtggaatt gtgagcggat aacaatttca cacaggaaac agctatgacc | 180 |

-continued

```
atgattacgc caagcgcgca attaaccctc actaaaggga acaaaagctg gagctccacc    240
gcggtggcgg ccgctctaga actagtggat ccaaagaatt cggcacgaga cccagtgacc    300
ttcaggcctg agagatttct tgaggaagat gttgatatta agggccatga ttacaggcta    360
ctgccattgg tgcagggcgc aggatctgcc ctggtgcaca attgggtatt aatttagttc    420
agtctatgtt gggacacctg cttcatcatt tcgtatgggc acctcctgag ggaatgaagg    480
cagaagacat agatctcaca gagaatccag ggcttgttac tttcatggcc aagcctgtgc    540
aggccattgc tattcctcga ttgcctgatc atctctacaa gcgacagcca ctcaattgat    600
caattgatct gatagtaagt ttgaattttg ttttgataca aaacgaaata acgtgcagtt    660
tctccttttc catagtcaac atgcagcttt ctttctctga agcgcatgca gctttctttc    720
tctgaagccc aacttctagc aagcaataac tgtatatttt agaacaaata cctattcctc    780
aaattgagwa tttctctgta ggggnngnta attgtgcaat ttgcaagnaa tagtaaagtt    840
tantttaggg nattttaata gtcctangta anangnggna atgntagngg gcattnagaa    900
anccctaata gntgttggng gnngntaggn tttttnacca aaaaaaaaa                949

<210> SEQ ID NO 5
<211> LENGTH: 959
<212> TYPE: DNA
<213> ORGANISM: Pinus radiata
<220> FEATURE:
<221> NAME/KEY: unsure
<222> LOCATION: (697)...(697)

<400> SEQUENCE: 5
gaattcggca cgagaaagcc ctagaatttt ttcagcatgc tatcacagcc ccagcgacaa     60 cttaactgc aataactgtg gaagcgtaca aaaagtttgt cctagtttct ctcattcaga    120
ctggtcaggt tccagcattt ccaaaataca cacctgctgt tgtccaaaga aatttgaaat    180
cttgcactca gccctacatt gatttagcaa acaactacag tagtgggaaa atttctgtat    240
tggaagcttg tgtcaacacg aacacagaga agttcaagaa tgatagtaat ttggggttag    300
tcaagcaagt tttgtcatct ctttataaac ggaatattca gagattgaca cagacatatc    360
tgaccctctc tcttcaagac atagcaagta cggtacagtt ggagactgct aagcaggctg    420
aactccatgt tctgcagatg attcaagatg gtgagatttt tgcaaccata aatcagaaag    480
atgggatggt gagcttcaat gaggatcctg aacagtacaa acatgtcag atgactgaat    540 atatagatac tgcaattcgg agaatcatgg cactatcaaa gaagctcacc acagtagatg    600
agcagatttc gtgtgatcat tcctacctga gtaaggtggg gagagagcgt tcaagatttg    660
acatagatga ttttgatact gttccccaga agttcanaaa tatgtaacaa atgatgtaaa    720
tcatcttcaa gactcgctta tattcattac tttctatgtg aattgatagt ctgttaacaa    780
tagtactgtg gctgagtcca gaaaggatct ctcggtatta tcacttgaca tgccatcaaa    840
aaaatctcaa atttctcgat gtctagtctt gattttgatt atgaatgcga cttttagttg    900
tgacatttga gcacctcgag tgaactacaa agttgcatgt aaaaaaaaaa aaaaaaaa     959

<210> SEQ ID NO 6
<211> LENGTH: 1026
<212> TYPE: DNA
<213> ORGANISM: Pinus radiata

<400> SEQUENCE: 6
gaattcggca cgagctttga ggcaacctac attcattgaa tcccaggatt tcttcttgtc     60
```

```
caaacaggtt taaggaaatg gcaggcacaa gtgttgctgc agcagaggtg aaggctcaga        120
caacccaagc agaggagccg gttaaggttg tccgccatca agaagtggga cacaaaagtc        180
ttttgcagag cgatgccctc tatcagtata tattggaaac gagcgtgtac cctcgtgagc        240
ccgagccaat gaaggagctc cgcgaagtga ctgccaagca tccctggaac ctcatgacta        300
cttctgccga tgagggtcaa tttctgggcc tcctgctgaa gctcattaac gccaagaaca        360
ccatggagat tggggtgtac actggttact cgcttctcag cacagccctt gcattgcccg        420
atgatggaaa gattctagcc atggacatca acagagagaa ctatgatatc ggattgccta        480
ttattgagaa agcaggagtt gcccacaaga ttgacttcag agagggccct gctctgccag        540
ttctggacga actgcttaag aatgaggaca tgcatggatc gttcgatttt gtgttcgtgg        600
atgcggacaa agacaactat ctaaactacc acaagcgtct gatcgatctg gtgaaggttg        660
gaggtctgat tgcatatgac aacaccctgt ggaacggatc tgtggtggct ccacccgatg        720
ctcccctgag gaaatatgtg agatattaca gagatttcgt gatggagcta acaaggccc         780 ttgctgtcga tccccgcatt gagatcagcc aaatcccagt cggtgacggc gtcacccttt        840
gcaggcgtgt ctattgaaaa caatccttgt ttctgctcgt ctattgcaag cataaaggct        900
ctctgattat aaggagaacg ctataatata tggggttgaa gccatttgtt ttgtttagtg        960
tattgataat aaagtagtac agcatatgca aagtttgtat caaaaaaaaa aaaaaaaaa       1020 aaaaaa                                                                 1026

<210> SEQ ID NO 7
<211> LENGTH: 1454
<212> TYPE: DNA
<213> ORGANISM: Pinus radiata

<400> SEQUENCE: 7
gaattcggca cgaggccaac tgcaagcaat acagtacaag agccagacga tcgaatcctg        60
tgaagtggtt ctgaagtgat gggaagcttg gaatctgaaa aaactgttac aggatatgca       120
gctcgggact ccagtggcca cttgtcccct tacacttaca atctcagaaa gaaaggacct       180
gaggatgtaa ttgtaaaggt catttactgc ggaatctgcc actctgattt agttcaaatg       240
cgtaatgaaa tggacatgtc tcattaccca atggtccctg gcatgaagt ggtggggatt        300 gtaacagaga ttggcagcga ggtgaagaaa ttcaaagtgg gagagcatgt aggggttggt       360
tgcattgttg ggtcctgtcg cagttgcggt aattgcaatc agagcatgga acaatactgc       420
agcaagagga tttggaccta caatgatgtg aaccatgacg gcacacctac tcagggcgga       480
tttgcaagca gtatggtggt tgatcagatg twtgtggttc gaatcccgga gaatcttcct       540
ctggaacaag cggcccctct gttatgtgca ggggttacag ttttcagccc aatgaagcat       600
ttcgccatga cagagcccgg gaagaaatgt gggattttgg gtttaggagg cgtggggcac       660
atgggtgtca agattgccaa agcctttgga ctccacgtga cggttatcag ttcgtctgat       720
aaaaagaaag aagaagccat ggaagtcctc ggcgccgatg cttatcttgt tagcaaggat       780
actgaaaaga tgatggaagc agcagagagc ctagattaca taatggacac cattccagtt       840
gctcatcctc tggaaccata tcttgccctt ctgaagacaa atggaaagct agtgatgctg       900
ggcgttgttc cagagtcgtt gcacttcgtg actcctctct taatacttgg gagaaggagc       960
atagctggaa gtttcattgg cagcatggag gaaacacagg aaactctaga tttctgtgca      1020
gagaagaagg tatcatcgat gattgaggtt gtgggcctgg actacatcaa cacggccatg      1080
```

```
gaaaggttgg agaagaacga tgtccgttac agatttgtgg tggatgttgc tagaagcaag    1140
ttggataatt agtctgcaat caatcaatca gatcaatgcc tgcatgcaag atgaatagat    1200
ctggactagt agcttaacat gaaagggaaa ttaaatttttt atttaggaac tcgatactgg    1260
tttttgttac tttagtttag cttttgtgag gttgaaacaa ttcagatgtt tttttaactt    1320
gtatatgtaa agatcaattt ctcgtgacag taaataataa tccaatgtct tctgccaaat    1380
taatatatgt attcgtattt ttatatgaaa aaaaaaaaa aaaaaaaaaa aaaaaaaaaa    1440
aaaaaaaaaa aaaa                                                     1454

<210> SEQ ID NO 8
<211> LENGTH: 740
<212> TYPE: DNA
<213> ORGANISM: Pinus radiata

<400> SEQUENCE: 8
gaattcggca cgagaccatt tccagctaat attggcatag caattggtca ttctatcttt     60
gtcaaaggag atcaaacaaa ttttgaaatt ggacctaatg tgtggaggc tagtcagcta    120 tacccagatg tgaaatatac cactgtcgat gagtacctca gcaaatttgt gtgaagtatg    180
cgagattctc ttccacatgc ttcagagata cataacagtt tcaatcaatg tttgtcctag    240
gcatttgcca aattgtgggt tataatcctt cgtaggtgtt tggcagaaca gaacctcctg    300
tttagtatag tatgacgagc taggcactgc agatccttca cacttttctc ttccataaga    360
aacaaatact cacctgtggt ttgttttctt tctttctgga actttggtat ggcaataatg    420
tctttggaaa ccgcttagtg tggaatgcta agtactagtg tccagagttc taagggagtt    480
ccaaaatcat ggctgatgtg aactggttgt tccagagggt gtttacaacc aacagttgtt    540
cagtgaataa ttttgttaga gtgtttagat ccatctttac aaggctattg agtaaggttg    600
gtgttagtga acggaatgat gtcaaatctt gatgggctga ctgactctct tgtgatgtca    660
aatcttgatg gattgtgtct ttttcaatgg taaaaaaaaa aaaaaaaaaa aaaaaaaaa    720 aaaaaaaaaa aaaaaaaaaa                                               740

<210> SEQ ID NO 9
<211> LENGTH: 624
<212> TYPE: DNA
<213> ORGANISM: Pinus radiata

<400> SEQUENCE: 9
gaattcctgc agcccggggg atccactagt tctagagcgg ccgccaccgc ggtggagctc     60
gcgcgcctgc aggtcgacac tagtggatcc aaagaattcg gcacgaggcc cgacggccac    120
ttgttggacg ccatggaagc tctccggaaa gccgggattc tggaaccgtt taaactgcag    180
cccaaggaag gactggctct cgtcaacggc acagcgtgg gatccgccgt ggccgcgtcc    240
gtctgtgttg acgccaacgt gctgggcgtg ctggctgaga ttctgtctgc gctcttctgc    300
gaggtgatgc aagggaaacc ggagttcgta gatccgttaa cccaccagtt gaagcaccac    360
ccagggcaga tcgaagccgc ggccgtcatg gagttcctcc tcgacggtag cgactacgtg    420
aaagaagcag cgcggcttca cgagaaagac ccgttgagca aaccgaaaca agaccgctac    480
gctctgcgaa catcgccaca gtggttgggg cctccgatcg aagtcatccg cgctgcyact    540
cactccatcg agcgggagat caattccgtc aacgacaatc cgttaatcga tgtctccagg    600
gacatggctg tccacggcgg caac                                          624
```

<210> SEQ ID NO 10
<211> LENGTH: 278
<212> TYPE: DNA
<213> ORGANISM: Pinus radiata

<400> SEQUENCE: 10

```
gaattcctgc agcccggggg atccactagt tctagagcgg ccgccaccgc ggtggagctc    60
cagtacctgg ccaaccccgt cacgactcac gtccagagcg ccgaacaaca caaccaggat   120
gtcaattccc tcggcttgat ctccgccaga aagactgccg aggccgttga gattttaaag   180
ctgatgttcg ctacatatct ggtggcctta tgccaggcga tcgatctccg gcacctggaa   240
gaaaacatgc gatccgttgt gaagcacgta gtcttgca                           278
```

<210> SEQ ID NO 11
<211> LENGTH: 765
<212> TYPE: DNA
<213> ORGANISM: Pinus radiata

<400> SEQUENCE: 11

```
gagctcctgc aagtcatcga tcatcagccc gttttctcgt acatcgacga tcccacaaat    60
ccatcatacg cgcttatgct ccaactcaga gaagtgctcg tagatgaggc tctcaaatca   120
tcttgcccag acgggaatga cgaatccgat cacaatttgc agcccgctga gagcgctgga   180
gctgctggaa tattacccaa ttgggtgttt agcaggatcc ccatatttca agaggagttg   240
aaggcccgtt tagaggaaga ggttccgaag gcgagggaac gattcgataa tggggacttc   300
ccaattgcaa acagaataaa caagtgcagg acatatccca tttacagatt cgtgagatca   360
gagttgggaa ccgatttgct aacagggccc aagtggagaa gccccggcga agatatagaa   420
aaggtatttg agggcatttg ccaagggaaa attggaaacg tgatcctcaa atgtctggac   480
gcttggggtg ggtgcgctgg accattcact ccacgtgcat atcctgcgtc tcctgcagcg   540
ttcaatgcct catattgggc atggtttgat agcaccaaat caccctctgc aacgagcggc   600
agaggttct  ggagcgccca acaacaacaa gttctttgat ttaactgact cttaagcatt   660
cctaaacagc ttgttcttcg caataacgaa tctttcatct tcgttacttt gtaaaagatg   720
gggttccaac aaaatagaag aaatattttc gatccaaaaa aaaaa                   765
```

<210> SEQ ID NO 12
<211> LENGTH: 453
<212> TYPE: DNA
<213> ORGANISM: Pinus radiata

<400> SEQUENCE: 12

```
tgattatgcg gatccttggg cagggatacg gcatgacaga agcaggcccg gtgctggcaa    60
tgaacctagc cttcgcaaag aatcctttcc ccgccaaatc tggctcctgc ggaacagtcg   120
tccggaacgc tcaaataaag atcctcgatt acaggaactg gcgagtctct cccgcacaat   180
caagccggcg aaatctgcat ccgcggaccc gaaataatga aggatatat  taacgacccg   240
gaatccacgc ccgctacaat cgatgaagaa ggctggctcc acacaggcga cgtcgggtac   300
attgacgatg acgaagaaat cttcatagtc gacagagtaa aggagattat caatataaag   360
gcttccaggt ggatcctgct aatcgaattc ctgcagcccg ggggtccact agttctagag   420
cggccgccac cgcggtggag ctccagcttt tgt                                453
```

<210> SEQ ID NO 13
<211> LENGTH: 278
<212> TYPE: DNA

-continued

```
<213> ORGANISM: Pinus radiata

<400> SEQUENCE: 13
tcttcgaatt ctctttcacg actgcttcgt taatggctgc gatggctcga tattgttaga      60
tgataactca acgttcaccg gagaaaagac tgcaggccca aatgttaatt ctgcgagagg     120
attcgacgta atagacacca tcaaaactca agttgaggca gcctgcagtg gtgtcgtgtc    180
agttgccgac attctcgcca ttgctgcacg cgattcagtc gtccaactgg ggggcccaac    240
atggacggta cttctgggag aaaagacgga tccgatca                            278

<210> SEQ ID NO 14
<211> LENGTH: 23
<212> TYPE: DNA
<213> ORGANISM: Pinus radiata

<400> SEQUENCE: 14
cttcgaattc wyttycayga ytg                                             23

<210> SEQ ID NO 15
<211> LENGTH: 22
<212> TYPE: DNA
<213> ORGANISM: Pinus radiata

<400> SEQUENCE: 15
gatcggatcc rtcyykycty cc                                              22
```